United States Patent [19]

Stehr et al.

[11] Patent Number: 5,412,136
[45] Date of Patent: May 2, 1995

[54] PROCESS FOR THE PREPARATION OF ALKYL SULFATE POWDER HAVING A HIGH BULK DENSITY

[75] Inventors: Michael Stehr, Gelsenkirchen; Adelbert Otte, Marl; Helmut Glaser, Gelsenkirchen; Hans-Josef Ratajczak, Marl; Klaus Schulze, Haltern, all of Germany

[73] Assignee: Huels Aktiengesellschaft, Marl, Germany

[21] Appl. No.: 106,623

[22] Filed: Aug. 16, 1993

[30] Foreign Application Priority Data

Aug. 17, 1992 [DE] Germany ................. 42 27 210.6

[51] Int. Cl.⁶ .......................... C07C 305/04
[52] U.S. Cl. .......................... 558/43
[58] Field of Search .................... 558/43, 39

[56] References Cited

U.S. PATENT DOCUMENTS 4,482,470 11/1984 Reuter et al. .

OTHER PUBLICATIONS

Database WPI, Derwent Publications Ltd., AN-79-70925B, JP-A-54 106 428, Aug. 21, 1979.
Patent Abstracts of Japan, vol. 1, No. 84, (C-77), JP-A-52 46 025, Dec. 4, 1977.
Chemical Abstracts, vol. 92, 1980, AN 24764c, Norihiro ONO, et al., "Granulation Of Higher Alkyl Sulfates", p. 143.

Primary Examiner—Nicky Chan
Attorney, Agent, or Firm—Oblon, Spivak, McClelland, Maier & Neustadt

[57] ABSTRACT

A process for the preparation of alkyl sulfate powders, which entails spraying an aqueous solution or dispersion of alkyl sulfates into a head part of a spraying tower through single-component nozzles under pressure sufficient to form a spray mist, and drying the resulting spray mist in co-current manner using an inert gas at a temperature sufficient to afford a powder having a bulk density of at least 300 g/l.

11 Claims, No Drawings

PROCESS FOR THE PREPARATION OF ALKYL SULFATE POWDER HAVING A HIGH BULK DENSITY

BACKGROUND OF THE INVENTION

1. Field of the Invention

The present invention relates to a process for the preparation of alkyl sulfate powders having a high bulk density.

2. Description of the Background

The alkali metal salts of monoalkyl half esters of sulfuric acid, called alkyl sulfates herein, contain an alkyl group of between 8 and 22 carbon atoms, and are of increasing interest as anaerobically degradable anionic surfactants.

Alkyl sulfates are obtained on an industrial scale by reacting alcohols with sulfur trioxide and then neutralizing the chemically labile half ester of sulfuric acid which is formed thereon using suitable aqueous bases, such as sodium hydroxide solution or aqueous sodium carbonate solution. The alkyl sulfates are produced as aqueous solutions, dispersions or pastes. These forms frequently make further processing difficult and are unsuitable for certain applications. For example, the presence of water, in particular, is found to be undesirable for many applications, requiring removal. Further, the additional weight of water adds considerable expense to the cost of transportation.

The removal of water, where required, can be effected in a variety of ways as long as the process used affords a solid which can be further processed with ease.

It is particularly advantageous to prepare alkyl sulphate powders from aqueous solutions since, in contrast to granules or flakes, for example, powders can be directly mixed with other powders to give final formulations and, in addition can be rapidly dissolved in water. In order to convert aqueous solutions of alkyl sulfates into powders, a plurality of processes are conceivable in principle. However, the process employed depends on both the physical and chemical properties of the alkyl sulfate solution to be dried and on the desired powder properties.

One such process is spray drying. For example, JP 54 10 6428 teaches such a process and that the alkyl sulfate slurries used must have a solids content of at least 60 to 80%, in order to be able to prepare powders having bulk densities above 200 g/l, which is, nevertheless, inadequate for further handling. Further, slurries having a surfactant content this high, according to the teaching of EP 0 084 154, can only be handled with equipment if particular measures are taken, such as the addition of additives of the same type. However, the substances which can be used for this purpose have certain disadvantages. They can, for example, impair the usability of the powders in a final formulation or, as a result of a low melting point, they can make the spraying, itself, difficult, since they promote clumping of the powders.

Thus, a need exists for alkyl sulfate powders having a high bulk density and which can be easily handled subsequent information.

SUMMARY OF THE INVENTION

Accordingly, it is an object of the present invention to provide an alkyl sulfate powder having a high bulk density.

It is also an object of the present invention to provide an alkyl sulfate powder which is easily handled after preparation.

The above objects and others are provided by an alkyl sulfate powder having a bulk density of at least 300 g/l.

DETAILED DESCRIPTION OF THE PREFERRED EMBODIMENTS

The present invention generally relates to a process for the preparation of alkyl sulfate powders having a high bulk density and alkyl sulfate powders produced thereby. Generally, the present process entails spray drying an aqueous solution or dispersion of alkyl sulfates having a solids content of about 10 to 60% by weight in a spraying tower, into the head part of which the liquid is sprayed by pressure through single-component nozzles and the spray mist thus resulting is dried by hot inert gas in co-current manner. Generally, the term "alkyl sulfates" as used herein means both alkyl sulfates having a uniform carbon number as well as mixtures of alkyl sulfates having a different carbon number in the alkyl chain.

Generally, the alkyl groups of the present alkyl sulfates have from 8 to 22 carbon atoms. However, alkyl groups having less than 8 carbon atoms, such as 6, for example, may be used. Further, alkyl groups having more than 22 carbon atoms, such as 24, for example, may be used. Nevertheless, it is preferred if 12 to 18 carbons are present in the alkyl groups.

Furthermore, the alkyl groups may be linear or branched, however, usually the alkyl groups are mixtures of different chain lengths as is customary for distillation "cuts" in surfactant chemistry.

The present invention provides alkyl sulfate powders having a bulk density of at least about 300 g/l starting from flowable, aqueous alkyl sulfate solutions or alkyl sulfate dispersions without the need for additives. This is achieved by a process in which aqueous solutions or dispersions of alkyl sulfates having a solids content from about 10 to 60% are sprayed into the head part of a spraying tower through single-component nozzles and the spray mist thus resulting is dried by hot inert gas in co-current manner.

Generally, as noted already, the aqueous solutions or dispersions of alkyl sulfates have a solids content of from about 10 to 60%, however, it is preferred if a solids content of about 20 to 50% is used. These are by weight percentages.

The aqueous solution or dispersion is atomized at a pressure between about $10^6$ and $10^7$ Pa into the spraying tower by means of commercial pressure nozzles. However, it is preferred if an atomization pressure of from about $2.5 \times 10^6$ to $5 \times 10^6$ Pa is used. All solutions of conventional sulfated fatty alcohol fractions are suitable as a feed for the atomization, as long as their viscosity permits pumping and atomization.

While any inert gas, such as argon, neon, krypton or xenon may be used, nitrogen is preferred as the inert gas for reasons of economy.

The present invention, thus, provides a process for the preparation of alkyl sulfate powders, wherein the aqueous solution or dispersion of alkyl sulfates is sprayed into the head part of a spraying tower through single-component nozzles under pressure and the spray mist thus resulting is dried in co-current fashion using hot inert gas to give a powder having a bulk density of at least about 300 g/l.

Generally, as a base material for the alkyl sulfates, fatty alcohol cuts are used, which are of petrochemical origin, however, they may also originate from natural oils and fats. For example, fatty alcohols from skin fat, coconut oil, palm oil and palm kernel oil may be used.

Furthermore, the spraying tower is generally operated in a direct or co-current manner.

The gas inlet/outlet temperatures are generally in the range of about 100° C. to 180° C. However, lower or higher temperatures may be used. Generally, the gas inlet temperature depends upon the feed quantity.

Additionally, single-component nozzles are commonly used in accordance with the present invention, and the effect of the present invention may be obtained using any type thereof. For example, a single component-hollow cone nozzle of the DELAVAN 2, 4P7 type may be used.

Generally, bulk densities of greater than 360 g/l may be achieved in accordance with the present invention. An important factor in determining the density obtained, however, is the viscosity of the aqueous solution.

Further, with respect to the water content, there is no bottom limit and the upper limit is determined by the flow behavior of the powder.

The following examples are provided solely for the purpose of illustration and are not intended to be limitative.

Example 1 and Comparison Example 1

A commercially-available 30% strength aqueous solution of coconut fatty alcohol sulfate ($C_{12}$-$C_{14}$) was used in a co-current tower operated by nitrogen to produce powders having the properties described in Table 1.

TABLE 1

|  | Example according to the invention | Comparison example |
|---|---|---|
| Spray conditions |  |  |
| Nozzle | Single-component-hollow cone nozzle | Two-component nozzle |
| Feed pressure | $10^6$ Pa (10 bar) | $3 \cdot 10^5$ Pa (3 bar) |
| Temperature of the gas for the atomization | Not applicable | 60° C. |
| Pressure of the gas for the atomization | Not applicable | $5 \cdot 10^5$ Pa |
| Gas inlet temperature | 155° C. | 155° C. |
| Gas outlet temperature | 115° C. | 115° C. |
| Inert gas amount (circulation gas) | 30 t $N_2$ | 30 t $N_2$ |
| Powder data |  |  |
| Bulk density | 360 g/l | 100 g/l |
| Water content by Karl Fisher | 1.7% | 1.2% |

From Table 1 above, it may be seen that an alkyl sulfate powder having a bulk density of 360 g/l was obtained, whereas the solution sprayed in a conventional manner using a two-component nozzle produced an alkyl sulfate having a bulk density of 100 g/l.

The drying of a commercially-available 30% strength aqueous solution of $C_{12}$-$C_{18}$-fatty alcohol sulfate in a co-current tower operated by nitrogen produced powders having properties described in Table 2.

TABLE 2

|  | Example according to the invention | Comparison example |
|---|---|---|
| Spray conditions |  |  |
| Nozzle | Single-component-hollow cone nozzle of the DELAVAN 2, 4 P7 type | Two-component nozzle DELAVAN |
| Feed pressure | $2 \cdot 10^6$ Pa (20 bar) | $3 \cdot 10^5$ Pa (3 bar) |
| Temperature of the gas for the atomization | Not applicable | 60° C. |
| Pressure of the gas for the atomization | Not applicable | $5 \cdot 10^5$ Pa |
| Gas inlet temperature | 150° C. | 148° C. |
| Gas outlet temperature | 117° C. | 118° C. |
| Inert gas amount (circulation gas) | 30 t $N_2$ | 30 t $N_2$ |
| Powder data |  |  |
| Bulk density | 320 g/l | 80 g/l |
| Water content by Karl Fisher | 1.67% | 1.2% |

The above Examples clearly indicate that the alkyl sulfate powders of the present invention exhibit a significant increase in bulk density.

Having now fully described the invention, it will be apparent to one of ordinary skill in the art that many changes and modifications can be made thereto without departing from the spirit or scope of the invention as set forth herein.

What is claimed as new and desired to be Secured by Letters Patent of the United States is:

1. A process for the preparation of alkyl sulfate powders, which comprises spraying an aqueous solution or dispersion of alkyl sulfates having a solids content of about 10 to 60% by weight into a head part of a spraying tower through single-component nozzles under a pressure sufficient to form a spray mist, and drying the resulting spray mist in a co-current manner using an inert gas at a temperature sufficient to afford a powder having a bulk density of from about 300 g/l to about 360 g/l.

2. The process of claim 1, wherein an admission pressure of liquid prior to spraying is about $10^6$ to $10^7$ Pa.

3. The process of claim 1, wherein the alkyl group of the alkyl sulfates is linear or branched and contains from about 8 to 22 carbon atoms.

4. The process of claim 3, wherein the alkyl group of the alkyl sulfates contains from about 12 to 18 carbon atoms.

5. The process of claim 1, wherein said powder produced has a bulk density of at least about 320 g/l.

6. The process of claim 1, wherein the aqueous solution or dispersion contains from about 20 to 50% by weight of alkyl sulfates.

7. The process of claim 1, wherein the inert gas used is nitrogen.

8. The process of claim 1, wherein an aqueous solution of 30% strength fatty alcohol sulfate of $C_{12}$-$C_{18}$ is used.

9. The process of claim 1, wherein a gas inlet temperature of inert gas is in the range of about 100° C. to 180° C.

10. The process of claim 1, wherein a gas outlet temperature of inert gas is in the range of about 100° C. to about 180° C.

11. The process of claim 2, wherein the pressure of said liquid is from about $2.5 \times 10^6$ to about $5 \times 10^6$ Pa.

* * * * *